(12) United States Patent
Poeze et al.

(10) Patent No.: US 9,510,779 B2
(45) Date of Patent: Dec. 6, 2016

(54) ANALYTE MONITORING USING ONE OR MORE ACCELEROMETERS

(75) Inventors: Jeroen Poeze, Mission Viejo, CA (US); Johannes Bruinsma, Mission Viejo, CA (US); Marcelo Lamego, Coto De Caza, CA (US)

(73) Assignee: MASIMO CORPORATION, Irvine, CA (US)

( * ) Notice: Subject to any disclaimer, the term of this patent is extended or adjusted under 35 U.S.C. 154(b) by 327 days.

(21) Appl. No.: 12/883,770

(22) Filed: Sep. 16, 2010

(65) Prior Publication Data

US 2011/0087083 A1  Apr. 14, 2011

Related U.S. Application Data

(60) Provisional application No. 61/243,507, filed on Sep. 17, 2009.

(51) Int. Cl.
*A61B 6/00* (2006.01)
*A61B 5/145* (2006.01)
(Continued)

(52) U.S. Cl.
CPC ....... *A61B 5/14532* (2013.01); *A61B 5/14551* (2013.01); *A61B 5/6838* (2013.01); *A61B 2562/0219* (2013.01); *A61B 2562/0233* (2013.01)

(58) Field of Classification Search
CPC .......................... A61B 5/0059; A61B 5/0084
USPC ......................................................... 600/476
See application file for complete search history.

(56) References Cited

U.S. PATENT DOCUMENTS

| 4,964,408 A | 10/1990 | Hink et al. |
| 5,041,187 A | 8/1991 | Hink et al. |

(Continued)

FOREIGN PATENT DOCUMENTS

| WO | WO 2006/050602 A1 | 5/2006 |
| WO | WO 2009/072024 A1 | 6/2009 |

OTHER PUBLICATIONS

US 8,845,543, 09/2014, Diab et al. (withdrawn)
(Continued)

*Primary Examiner* — Tse Chen
*Assistant Examiner* — Hien Nguyen
(74) *Attorney, Agent, or Firm* — Knobbe, Martens, Olson & Bear, LLP

(57) ABSTRACT

The present disclosure relates to methods, devices, and systems for measuring a blood analyte, such as glucose. The disclosure relates more specifically to the use in such methods, devices, and systems of one or more accelerometers to aid in the collection of data, operation of the device, filtering, and other uses. In some embodiments, the accelerometers are three-dimensional accelerometers. An accelerometer can be used in conjunction with analyte monitoring that may be performed with infrared, near infrared, or other wavelength spectroscopy. The accelerometer may allow a monitoring instrument to expect noisy measurement data, indicate positioning of a measurement site for improved expected results, indicate position of the instrument, or help the user properly place or control the instrument. It may also improve analyte monitoring by providing motion information that can be used to help determine and reduce or remove movement-related signal artifacts or noise that may be present within the monitoring signal.

13 Claims, 9 Drawing Sheets

(51) Int. Cl.
*A61B 5/1455* (2006.01)
*A61B 5/00* (2006.01)

(56) References Cited

U.S. PATENT DOCUMENTS

| | | | |
|---|---|---|---|
| 5,069,213 A | 12/1991 | Polczynski |
| 5,337,744 A | 8/1994 | Branigan |
| 5,341,805 A | 8/1994 | Stavridi et al. |
| 5,377,676 A | 1/1995 | Vari et al. |
| 5,452,717 A | 9/1995 | Branigan et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,921,367 B2 * | 7/2005 | Mills ........................... 600/481 |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |

(56) References Cited

U.S. PATENT DOCUMENTS

| | | |
|---|---|---|
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,089,455 B1 * | 1/2012 | Wieder ............... 345/156 |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |

(56) References Cited

U.S. PATENT DOCUMENTS

| | | |
|---|---|---|
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,494,507 B1 * | 7/2013 | Tedesco et al. ............... 455/418 |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,084,569 B2 | 7/2015 | Weber et al. |
| 2002/0165462 A1 * | 11/2002 | Westbrook et al. ........... 600/529 |
| 2003/0149348 A1 * | 8/2003 | Raskas ........................... 600/310 |
| 2003/0216754 A1 * | 11/2003 | Kraemer et al. ............... 606/142 |
| 2004/0133079 A1 | 7/2004 | Mazar et al. |
| 2006/0074313 A1 * | 4/2006 | Slayton et al. ................. 600/439 |
| 2008/0228084 A1 * | 9/2008 | Bedard et al. ................. 600/477 |
| 2008/0312709 A1 | 12/2008 | Volpe et al. |

(56) References Cited

U.S. PATENT DOCUMENTS

| | | |
|---|---|---|
| 2009/0015695 A1* | 1/2009 | Dunki-Jacobs et al. ...... 348/241 |
| 2009/0054742 A1* | 2/2009 | Kaminska et al. ........... 600/301 |
| 2010/0261979 A1 | 10/2010 | Kiani |
| 2011/0001605 A1 | 1/2011 | Kiani et al. |
| 2011/0040962 A1* | 2/2011 | Peyre ........................... 713/100 |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

OTHER PUBLICATIONS

Kim, sang H. et al., "Adaptive Noise Cancellation Using Accelerometers for the PPG Signal from Forehead," Engineering in Medicine and Biology Society, 29th Annual International Conference of the IEEE, Aug. 23-26, 2007, pp. 2564-2567.

PCT International Search Report, App. No. PCT/US 2010/049190, Date of Actual Completion of Search: Nov. 29, 2010, 5 pages.

* cited by examiner

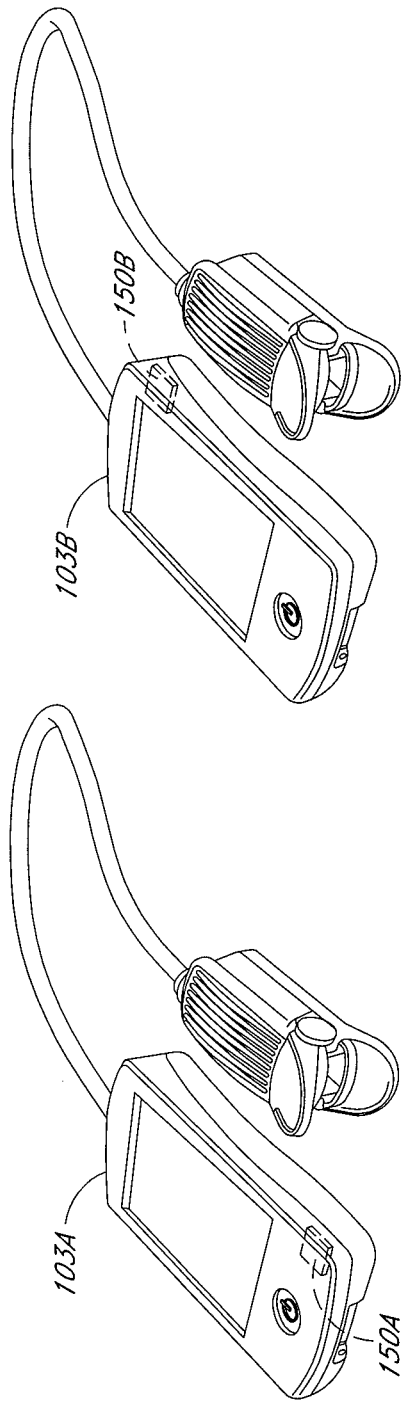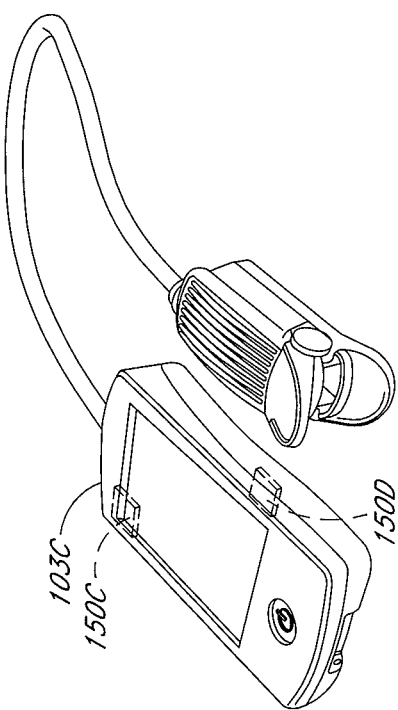

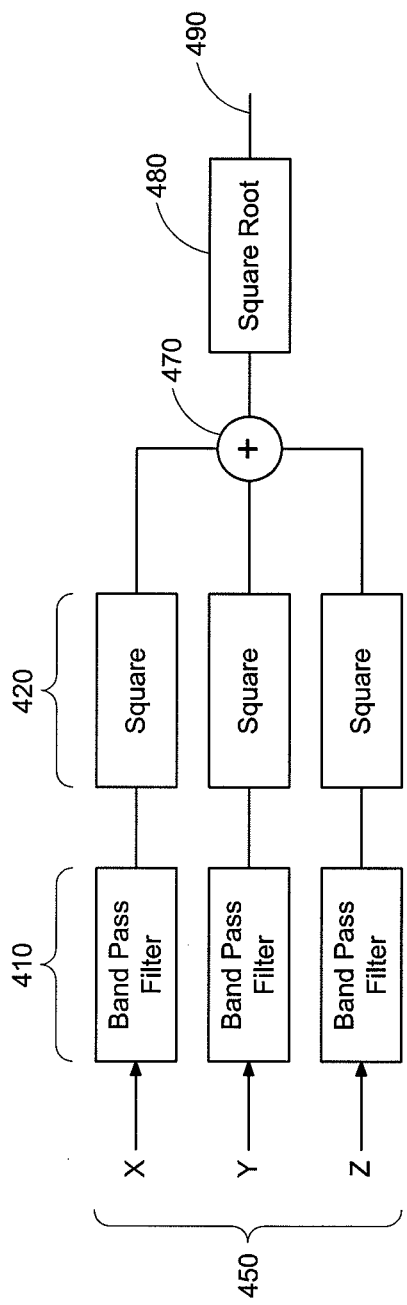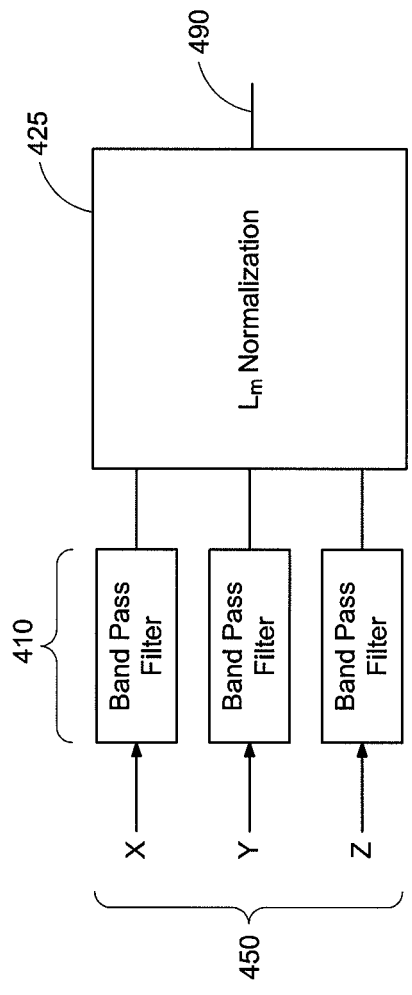
FIG. 4A
FIG. 4B

ANALYTE MONITORING USING ONE OR MORE ACCELEROMETERS

REFERENCE TO RELATED APPLICATIONS

The present application claims priority benefit under 35 U.S.C. §119 (e) from U.S. Provisional Application No. 61/243,507, filed Sep. 17, 2009, entitled "Improving Analyte Monitoring Using One Or More Accelerometers," which is incorporated herein by reference.

FIELD

The present disclosure relates to measuring a blood analyte, such as glucose. The disclosure relates more specifically to the use in such measurements of an accelerometer to aid in the collection of data, operation of the device, filtering, and other uses.

BACKGROUND

Measuring blood analytes, such as oxygen, carbon monoxide, methemoglobin, total hemoglobin, glucose, proteins, glucose, lipids, a percentage thereof (e.g., saturation) and other physiologically relevant patient characteristics can be difficult. Consider for example, the measurement of blood glucose. Invasive techniques used to measure glucose levels can be painful and inconvenient to perform. In addition, some patients, such as elderly or infant patients, cannot reliably perform these invasive tests on their own. These shortcomings can be especially significant in diabetic patients who require frequent monitoring. Failure to properly monitor and control blood glucose level can have serious consequences for a diabetic patient.

Considerable efforts have been made to develop noninvasive techniques for measuring blood glucose. For example, one noninvasive technique that has been attempted is infrared spectroscopy. With infrared spectroscopy, blood glucose is measured based on the amount of optical radiation absorbed, transmitted, or reflected from the patient's tissue.

Unfortunately, blood glucose can be difficult to measure using traditional infrared spectroscopy. Biologic tissue and water have a high intrinsic absorption at the same wavelengths of light that are responsive to blood glucose. Blood glucose also exists in relatively low concentrations. Furthermore, different patients will have large variations in the optical properties of their skin and blood composition. In addition, any physical movement of the measurement site introduces noise in the measurement signal, making an accurate reading very difficult. These and other challenges have made noninvasive glucose monitoring difficult.

The issues exist beyond the measurement of glucose. In certain conditions, similar problems may exist for the measurement of other analytes, such as oxygen, carbon monoxide, methemoglobin, total hemoglobin, glucose, proteins, glucose, lipids, a percentage thereof (e.g., saturation) or for measuring many other physiologically relevant patient characteristics.

SUMMARY

The present disclosure relates to methods, devices, and systems for measuring a blood analyte, such as glucose. The disclosure relates more specifically to the use in such methods, devices, and systems of one or more accelerometers to aid in the collection of data, operation of the device, filtering, and other uses. In some embodiments, the accelerometer is a three-dimensional ("3D") accelerometer.

The term 3D accelerometer as used herein includes its broad meaning known to a skilled artisan. Accelerometers may provide outputs responsive to acceleration of the device and three orthogonal axes, sometimes denoted the "X," "Y," and "Z" axes. As discussed herein, an accelerometer can be used in conjunction with analyte monitoring that may be performed with infrared, near infrared, or other wavelength spectroscopy. For example, the processing of data from an accelerometer may allow a monitoring instrument to expect noisy measurement data, indicate position of a measurement site for improved expected results, indicate position of the instrument, a combination of the same and the like. In some embodiments, the use of an accelerometer may improve analyte monitoring by providing motion information that can be used to help determine movement-related signal artifacts or noise that may be present within the monitoring signal. In some embodiments, a 3D accelerometer is used to provide greater detail of the motion noise. The removal of artifacts and noise may improve the quality of the analyte monitoring signal. Additionally, in some embodiments, the information from the accelerometers can also be used to provide feedback to the patient, subject, or user of the device in order to aid them in, for example, moving the sensor to the correct position or orientation or keeping the sensor motionless or nearly motionless. In various embodiments, accelerometers can also be placed on the base or processing unit of the device to enable control of said device using device-centric motion.

BRIEF DESCRIPTION OF THE DRAWINGS

FIGS. 3A, 3B, and 3C illustrate the optional placement of accelerometers 150A, 150B, 150C, and 150D in varied locations in devices 103A, 103B, and 103C.

FIG. 4A is a block diagram depicting a first system for processing accelerometer data.

FIG. 4B is a block diagram depicting a second system for processing accelerometer data.

DESCRIPTION OF EMBODIMENTS

Generally, certain embodiments disclosed herein may include an analyte measuring system connected to a device designed to process the signal sent out from the sensor. Each of the sensor and the device may have thereto attached one or more accelerometers. The accelerometers may be used to provide information to the system. For example, the accelerometer or accelerometers on the sensor may be used to indicate that the signal coming from the sensor is noisy or to indicate to the patient that his or her finger is not in the correct position or orientation, such as the finger being level and being below the patient's heart, with the location of the finger relative to the patient's heart being estimated, for example, from the orientation of the sensor and knowledge of the mechanics of the shoulder, elbow, wrist, and fingers. The device may also provide the user feedback on the movement of the sensor. When it is important that the user control or cease movement of the sensor, such feedback on movement of the sensor can be useful to control or cease movement and thereby improve the measurement accuracy. As another example, the accelerometer or accelerometers on the device may be used to control the device. The accelerometers on the device may be used to indicate the orientation of the device using a 3D object on the display of the device, shaking the device may clear the screen on the device, and other examples discussed herein.

Figure 1:
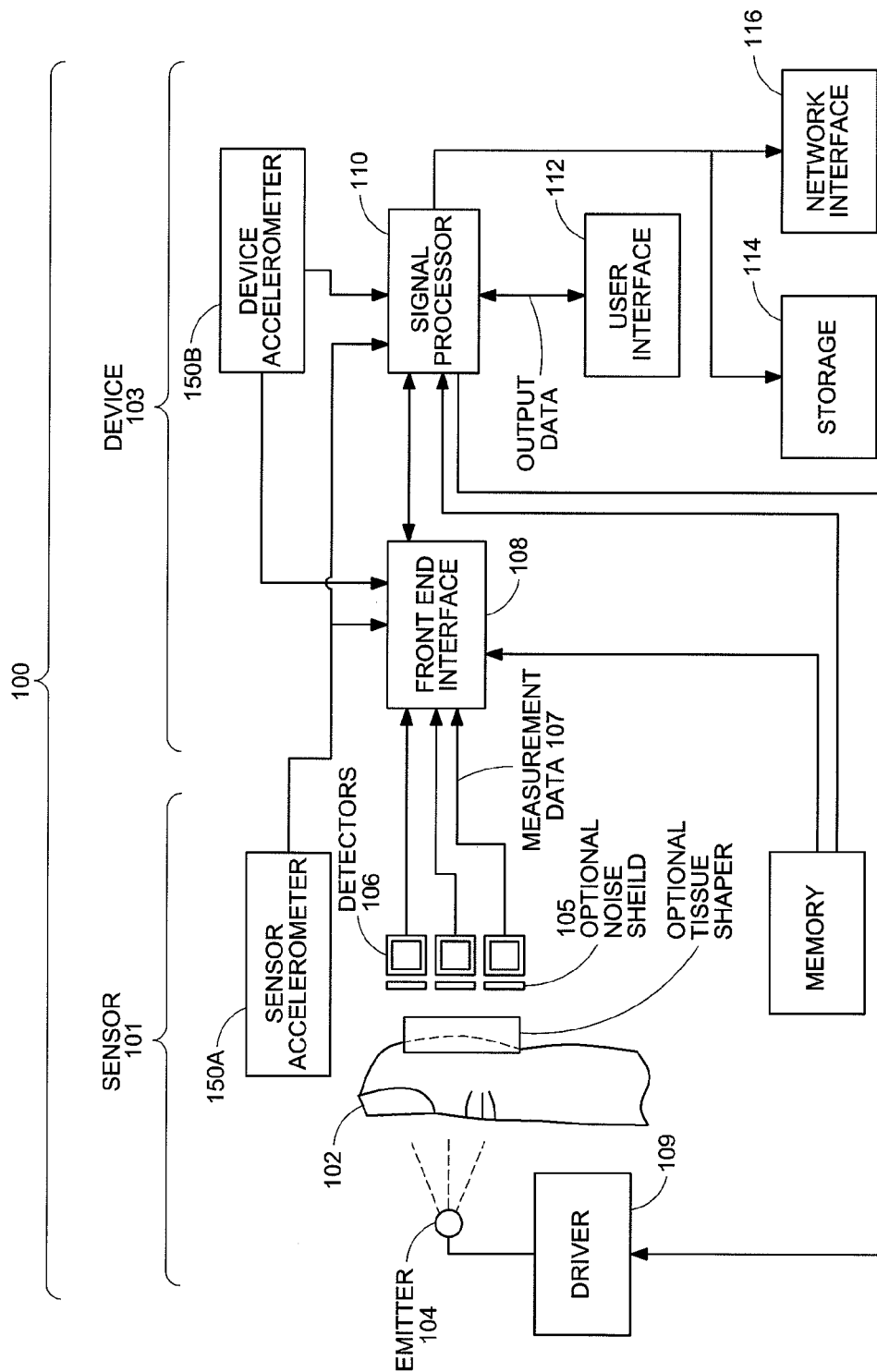
FIG. 1 is a block diagram of an exemplary data collection system capable of noninvasively measuring one or more blood analytes in a monitored patient, including one or more accelerometers, according to an embodiment of the disclosure.
Figure 2A:
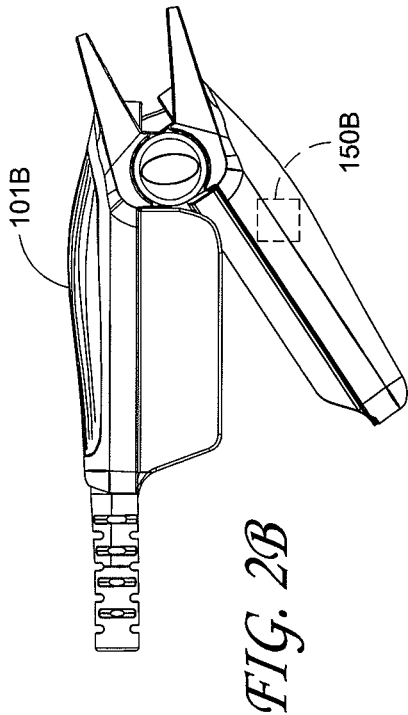
FIGS. 2A, 2B, 2C, and 2D illustrate optional placements of accelerometers 150A, 150B, 150C, 150D, and 150E in varied locations in sensors 101A, 101B, 101C, and 101D.
Figure 2C:
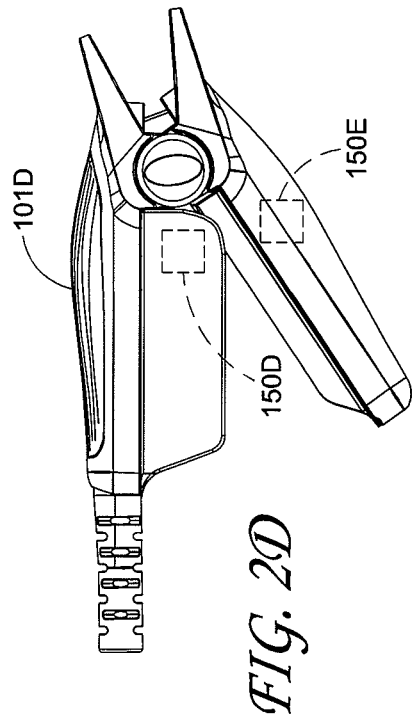
Figure 2B:
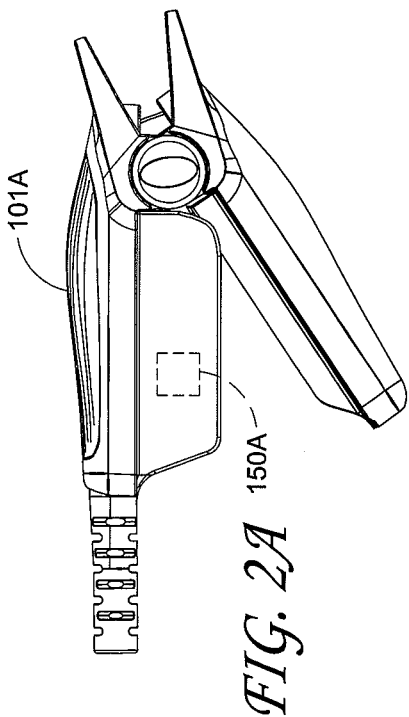
Figure 2D:
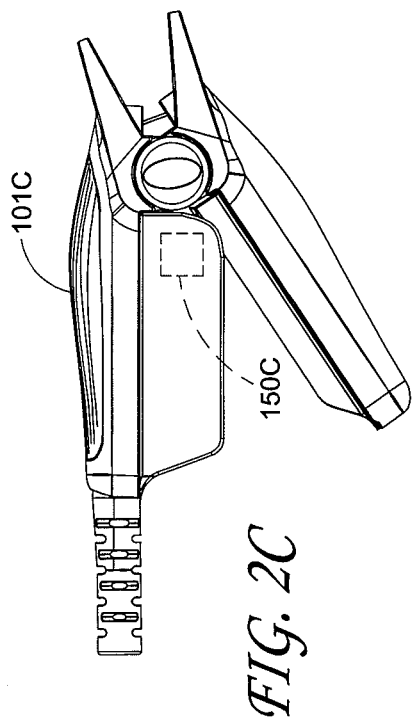

The remainder of the disclosure refers to the embodiments disclosed in the figures. For example, FIG. 1 illustrates an exemplary data collection system 100. System 100 can be configured to noninvasively measure blood analytes, such as glucose, total hemoglobin, methemoglobin, oxygen content, etc. System 100 may be capable of measuring optical radiation from the measurement site. For example, in some embodiments, system 100 may employ photodiodes defined in terms of area from about 1 mm$^2$–5 mm$^2$ (or higher) that are capable of detecting about 100 nanoamps (nA) or less of current resulting from measured light at full scale. An artisan will recognize from the disclosure herein that the phrase "at full scale" includes its ordinary meaning, which includes light saturation of the photodiode amplifier.

The artisan will also recognize from the disclosure herein, that the system 100 may measure a range of about 2 nA to about 100 nA full scale. System 100 may also include sensor front-ends that are capable of processing and amplifying current from the detector(s) at signal-to-noise ratios (SNRs) of about 100 decibels (dB) or more, e.g., about 120 dB in order to measure various desired analytes. An artisan will recognize that system 100 may operate with a lower SNR, if improved accuracy is desired for an analyte like glucose.

As shown in FIG. 1, the data collection system 100 may be configured to measure glucose concentrations based on detection of light attenuated by a measurement site 102. Measurement site 102 may be any location on patient's body, such as a finger, ear lobe, and the like. In other embodiments, the system 100 may measure various blood analytes, other physiological parameters, or other data or collection of data useful in determining a state or trend of wellness of a patient. As shown in FIG. 1, the system 100 may include an optional tissue thickness adjuster or tissue shaper, such as a protrusion, bump, or other suitable tissue shaping mechanism. In an embodiment, the tissue shaper seeks to create a substantially flat surface proximate to the finger and apply sufficient pressure to cause the finger tissue to be flat. In an embodiment, the shaper balances the performance enhancement caused by reducing the finger thickness, with the desire to avoid occlusion or perhaps even attempt to avoid disrupting blood flow at all.

FIG. 1 also illustrates an optional noise shield 105. In an embodiment, the noise shield 105 may advantageously be adapted to reduce electromagnetic noise while attempting to increase the transmittance or minimize attenuation of light from the measurement site 102 to the detectors 106. For example, the shield 105 may advantageously comprise a conductive coated glass or metal grid electrically communicating with one or more other shields of the sensor 101. In an embodiment where the shield 105 comprises conductive coated glass, the coating may advantageously comprise indium tin oxide. In an embodiment, the indium tin oxide comprises a surface resistivity ranging from approximately 30 ohms per square inch to 500 ohms per square inch, or, in some embodiments, approximately 30, 200, or 500 ohms per square inch. Other conductive materials substantially transparent to light will be recognizable to an artisan from the disclosure herein.

In some embodiments, system 100 may be configured to measure blood analytes like glucose at measurement sites somewhere along a non-dominant arm or from a patient's non-dominant hand, e.g., a right-handed person's left arm or left hand. In some patients, the non-dominant arm or hand may have less musculature and higher fat content, which can result in less water content in that tissue of the patient. Tissue having less water content may provide less interference with the particular wavelengths that are absorbed in a useful manner by blood analytes like glucose. Accordingly, in some embodiments, system 100 may be configured for use on a person's non-dominant hand or arm.

Data collection system 100 may comprise one or more sensors, such as a sensor 101, that is coupled to a processing device 103. In an embodiment, sensor 101 and device 103 may be integrated together into a single unit like a handheld device. In an embodiment, sensor 101 and device 103 may be separate from each other and communicate with one with another in any suitable manner, such as, for example, through wired or wireless communications, over one or more computing networks, combinations of the same, or the like. The sensor 101 and device 103 may be attachable and detachable from each other for the convenience of the user or caregiver, for ease of storage, sterility issues, or the like. Sensor 101 and device 103 will now be further described.

As shown in FIG. 1, sensor 101 may comprise an emitter 104, an optional tissue thickness adjuster, a set of detectors 106, and optionally, one or more optional front-end interfaces 108 (not pictured). Emitter 104 may serve as the source of optical radiation transmitted towards measurement site 102. In some embodiments, emitter 104 is configured as a optical point source, and thus, the optical sources of emitter 104 may be located within a relatively close distance to each other, such as within about a 2 mm to about 4 mm diameter; however, an artisan will recognize from the disclosure herein other relative spatial relationships that effectively behave as a point source from the perspective of one or more photodetectors. In an embodiment, emitter 104 may comprise sets of optical sources that are capable of emitting visible and near-infrared optical radiation.

An artisan will also recognize that other wavelength centroids or ranges may be useful in system 100 for distinguishing other types of tissue, fluids, tissue properties, fluid properties, combinations of the same, or the like. Disclosure of considerations and embodiments of wavelengths of light and emitters and receivers are disclosed in related U.S. Provisional Patent Application, Ser. No. 61/078,228, filed Jul. 3, 2008 to Kiani et al., incorporated herein in its entirety by reference and specifically incorporated as to disclosure related to foregoing considerations and other processing techniques.

In an embodiment, driver 109 drives emitter 104. For example, driver 109 may be configured to provide pulses of current to emitter 104. In some embodiments, driver 109 is capable of driving emitter 104 to emit optical radiation in a pattern that varies by less than about 10 parts-per-million; however an artisan will also recognize from the disclosure herein other amounts of variation.

Detectors 106 capture and measure light from measurement site 102. For example, detectors 106 may capture and measure light transmitted from emitter 104 that has been attenuated or reflected from the tissue in measurement site 102. Detectors 106 may then provide a detector signal 107 to indicate the light captured or measured. Detectors 106 may be implemented using one or more photodiodes. Many types of photodiodes are well known to an artisan, and from the disclosure herein, the artisan will recognize many different types of photodiodes may be used to emphasize that particular photodiode's design specifications, response attributes or the like. A skilled artisan will also recognize that a system for emission and capture of light could be built with small modifications to the above using photo conductors or photo resisters.

In addition, detectors 106 may be arranged with spatial considerations also discussed in the foregoing incorporated application, which is also specifically incorporated for subject matter relating to detection and other considerations.

Front-end interfaces 108 provide an interface that adapts the output of detectors 106, which is responsive to desired physiological parameters. For example, front-end interfaces 108 may adapt signal 107 from detectors 106 into a form that can be handled by device 103, or signal processor 110 in device 103. As shown in FIG. 1, front-end interfaces 108 may have components assembled in sensor 101, device 103, connecting cabling when relevant, combinations of the same, or the like. These embodiments may be chosen based on various factors including space desired for the components, desired noise reductions or limitations, desired heat maximums of the front-end interfaces, or the like.

The front-end interfaces 108 may also be connected to one or more accelerometers 150A and 150B. The front-end interface 108 may process the output from the accelerometers 150A and 150B in order to produce signals in a form that can be handled by the signal processor 110. Alternatively, the accelerometers 150A and 150B may be connected to and provide a signal directly to the signal processor 110. Accelerometer 150A may be coupled to or encased within sensor 101 or its housing. Accelerometer 150B may be coupled to or encased within device 103 or its housing. As depicted in FIGS. 2A-2D and 3A-3C, in some embodiments, one or more additional accelerometers 150A-150E may be associated with one or both of the sensor 101 and device 103 and may be placed in various positions.

The foregoing front-end interfaces 108 may be coupled to detectors 106, signal processor 110, and accelerometers 150A and 150B using a bus, wire, wireless, electrical or optical cable, flex circuit, or some other form of signal connection. An artisan may also recognize that front-end interfaces 108 may be at least partially integrated with other components, such as detectors 106 and/or accelerometers 150A or 150B. For example, front-end interfaces 108 may comprise integrated circuits that are on the same circuit board as detectors 106. Other configurations will be recognized by an artisan.

Considerations of specific exemplary embodiments of front-end interfaces 108 herein may parallel the considerations in specific embodiments of front-end interfaces 108 as disclosed in the incorporated application referred to above and the like.

As shown in FIG. 1, device 103 may comprise a front-end interface 108, a signal processor 110, and a user interface, such as a user interface 112. Device 103 may also comprise optional outputs alone or in combination with user interface 112, such as storage 114 and a network interface 116. In an embodiment, signal processor 110 comprises the processing logic that determines measurements for desired analytes, such as glucose, based on the streams of signals from detectors 106. Signal processor 110 may be implemented using known technology, such as application specific integrated circuits, field programmable gate arrays, and other available processors. An artisan will recognize from the disclosure herein that signal processor 110 may comprise a number of processors and sub-processors to perform its functions.

In addition, signal processor 110 may provide various signals that control the operation of sensor 101. For example, signal processor 110 may provide an emitter control signal to driver 109 for emitter 104. As also shown, an optional memory communicates with front-end interface 108, sensor 101, device 103, and/or signal processor 110. This memory may serve as a buffer or storage location for front-end interface 108 or signal processor 110. An artisan will recognize many uses for such a memory, including program or partial program storage, quality control measures, upgrade capability, or the like.

User interface 112 serves as a user interface component and provides an output, for example, to a user of system 100. User interface 112 may be implemented using well known components, such as a touch-screen display, a liquid crystal display (LCD), and organic light emitting diode (LED) display. In addition, user interface 112 may be manipulated to allow for measurement on the non-dominant side of patient. For example, user interface 112 may include a flip screen, a screen that can be moved from one side or another on device 103, or may include an ability to reorient its display indicia responsive to user input or device orientation.

Device 103 may execute various software and applications to provide results to the user, the results provided in a known or recognizable manner. Artisans will also recognize from the disclosure herein that system 100 may be provided without a display and simply provide an output signal to a separate display or system.

Storage 114 and network interface 116 represent other optional output connections that may be implemented. For example, system 100 may be coupled to storage 114 that is in the form of a hard disk, flash memory card, or other suitable computer accessible memory. System 100 may also comprise a network interface 116, such as a serial bus port, an Ethernet port, a wireless interface, or other suitable communication device(s) that allows system 100 to communicate and share data with other devices. Device 103 may comprise various other components, such as a general purpose processor or controller (not shown) to provide a user interface, control data communications, data trending computations, or other suitable data displays, whether indicative to individual parameter measurements or combined or aggregated data displays.

Although disclosed with reference to FIG. 1, an artisan will recognize from the disclosure herein that the system 100 may include other components or may be configured in different ways. For example, system 100 may include a touch screen that is used by the user to control the operation of device 103. In addition, system 100 may be configured with both the emitter 104 and detectors 106 on the same side of the measurement site 102. System 100 may also include a sensor that measures the power of light emitted from emitter 104. System 100 may also integrate the sensor and its front-end interfaces into the same component. Alternatively, the sensor and its front-end interfaces may be provided in different components of system 100.

FIGS. 2A, 2B, 2C, and 2D illustrate optional placements of accelerometers 150A, 150B, 150C, 150D, and 150E in varied locations in sensors 101A, 101B, 101C, and 101D. An accelerometer 150A, 150B, 150C, 150D, or 150E may measure acceleration that it experiences relative to gravity or freefall. An accelerometer 150A, 150B, 150C, 150D, or 150E may provide acceleration information along three axes and may provide acceleration information which is the equivalent of inertial acceleration minus local gravitational acceleration. Accelerometers 150A, 150B, 150C, 150D, and 150E are well known to those skilled in the art. They may be micro-electromechanical systems and may include piezoresistors. The accelerometers 150A, 150B, 150C, 150D, and 150E may be high impedance charge output or low impedance output accelerometers. In some embodiments, accelerometers 150A, 150B, 150C, 150D, and 150E may be tri-axis accelerometers and the output of the accelerometers 150A, 150B, 150C, 150D, and 150E may include three signals each of which represents acceleration in particular axis. The output of accelerometers 150A, 150B, 150C, 150D, and 150E may be 8 bit, 12 bit, or any other appropriate-sized output signal. The outputs of the accelerometers may be analog or digital.

The accelerometers 150A, 150B, 150C, 150D, and 150E may be used to determine whether the portion of the patient to which the sensor 101A, 101B, 101C, or 101D is attached is in the correct position, such as a digit being level and positioned below the heart of patient, or to see whether the sensor 101A, 101B, 101C, or 101D is moving so much as to cause a signal obtained from the sensor to be too noisy to be accurate. The signals from the accelerometers 150A, 150B, 150C, 150D, and 150E may then be used to help guide the patient in placing and steadying the sensor 101A, 101B, 101C, or 101D.

As depicted in these figures, one or more accelerometers 150A, 150B, 150C, 150D, and 150E can be placed in various positions in a sensor 101A, 101B, 101C, or 101D. In some embodiments, the accelerometers 150A, 150B, 150C, 150D, and 150E may be placed on the sensors 101A, 101B, 101C, and 101D in such a way that during motion of a sensor 101A, 101B, 101C, or 101D, the accelerometers 150A, 150B, 150C, 150D, and 150E are subject to the same or similar acceleration as the measurement site. For example, on a digit, sensor 101A, 101B, 101C, or 101D, the accelerometers 150A, 150B, 150C, 150D, and 150E might be placed near an emitter and/or detector close to the tip of the finger. For a forehead or ear sensor 101A, 101B, 101C, or 101D, the accelerometers 150A, 150B, 150C, 150D, and 150E might be placed near either the detector or emitter on the sensor 101A, 101B, 101C, or 101D.

FIGS. 3A, 3B, and 3C illustrate optional placements of accelerometers 150A, 150B, 150C, and 150D in varied locations on or in devices 103A, 103B, and 103C. The accelerometers 150A, 150B, 150C, and 150D on the devices 103A, 103B, and 103C may be similar to those described above. The accelerometers 150A, 150B, 150C, and 150D on the devices 103A, 103B, and 103C may allow the device to produce a 3D object that shows the relative orientation of the device 103A, 103B, and 103C. In some embodiments, for example, if the user looks up at the bottom of device 103A, 103B, and 103C, then the user may see the bottom of the 3D object. In some embodiments, the devices 103A, 103B, and 103C allow a person to make notations or to take notes. The accelerometers 150A, 150B, 150C, and 150D on the devices 103A, 103B, and 103C may allow one to clear a screen on the device 103A, 103B, and 103C by shaking the device 103A, 103B, and 103C. In some embodiments, the devices 103A, 103B, and 103C may also speak parameters that are displayed or displayable on the devices 103A, 103B, and 103C, such as date, measurements, and time.

FIG. 4A is a block diagram depicting a first system for processing accelerometer data. In some embodiments, the output signal or signals 450 of a 3D accelerometer are received at separate band pass filters 410, one for each component of signal 450 or for each separate signal 450. The band pass filters 410 may be low pass filters 410. As discussed above, the output signals 450 may comprise 8 bit, 12 bit, or any other appropriately-size output signal(s) if it is digital. The output signal 450 may also be analog. The output signals 450 may also include any other set or compilation of data that allows it to indicate a 3D acceleration. The band pass filters 410 may operate to remove low frequency acceleration changes from the output signals 450. Some 3D accelerometers may have a drift. That is, the 3D accelerometers may indicate a slow change over time that is not actually occurring. Passing the output signals 450 through the band pass filters 410 (embodied as low pass filters 410) may remove the drift from the accelerometers. The output of the band pass filters 410 may be fed into squaring mechanisms 420. The squaring mechanisms 420 may square the outputs of the band pass filters 410. The outputs of the squaring mechanisms 420 may be combined in combination mechanism 470. In some embodiments, the combination performed in combination mechanism 470 is a summation of the signals. The combination performed may also include combining the squared components into a vector. After the outputs of the squaring mechanisms 420 had been combined by combination mechanism 470. The square root mechanism 480 may take the square root of the combination. The output of the square root mechanism 480 is a filtered acceleration signal 490.

FIG. 4B is a block diagram depicting a second system for processing accelerometer data. FIG. 4B is similar to FIG. 4A in that each takes output signals 450 and applies band pass filters 410. The difference between the two figures is that in FIG. 4B an $L_m$ normalization unit 425 processes output signal 450 in order to produce filtered acceleration signal 490. A general equation for $L_m$ normalization may be:

$$|x|_m = (\Sigma_{k=1}^{n} |x_k|^m)^{1/m},$$

Where m is the level of normalization and n is the number of component or 'x' signals. The system depicted in FIG. 4A may be equivalent to an $L_2$ normalization, where x=3. In some embodiments, if m=1, then the result is the sum of the absolute values of $x_k$. If m=∞, then the result may be the maximum absolute value of $x_k$.

In some embodiments, such as that depicted in FIG. 4B, output signal 450 is processed by band pass filters 410 and the output of those filters are processed by the $L_m$ normalization unit 425, which in turn produces filtered acceleration signal 490. The choice of value for the "m" for the $L_m$ normalization unit 425 will depend on the needs of the system, the type of noise expected or found in the system, available and preferable hardware, and other considerations known to those skilled in the art.

The filtered acceleration signal 490 in both FIGS. 4A and 4B may indicate the acceleration of the 3D accelerometers in question. As discussed above, in some embodiments, the filtered acceleration signal may be used to indicate that a sensor is moving too much and causing too much noise in the signal for the signal to be trusted. The filtered acceleration signal 490 may also be used to remove noise from a recorded signal. In some embodiments, when a captured analyte signal is graphed, the color of the signal may be change based on the filtered acceleration signal. For example, the analyte signal may be colored red if much noise is detected with the filtered acceleration signal 490, yellow if there is only moderate noise, and green if there is little noise. In some embodiments, if there is low perfusion of blood, then the signal may be weak because it is hard to measure the oxygen or other analyte in the blood. If this is the case, then even a small amount of motion in the sensor, as detected with the filtered acceleration signal 490, may indicate a bad reading and may warrant graphing the analyte signal in red. If the perfusion is high, however, and even if some motion is detected with filtered acceleration signal 490, then the graph might still be colored green. As noted herein, the filtered acceleration signal 490 may also be used to interact with the user interface of the device or otherwise control a sensor or accompanying device.

In some embodiments, the analyte signal and the filtered acceleration signal 490 from the sensor may be graphed together. This may allow a user to visually receive feedback that she should reduce or eliminate movement of the sensor if the signal is too noisy.

In the embodiments where the filtered acceleration signal 490 is a vector, orientation may be obtainable. Orientation may be useful, as discussed above, because it will allow the system to indicate to user that the finger on which the sensor is attached is not level or otherwise oriented correctly.

Figure 5A:
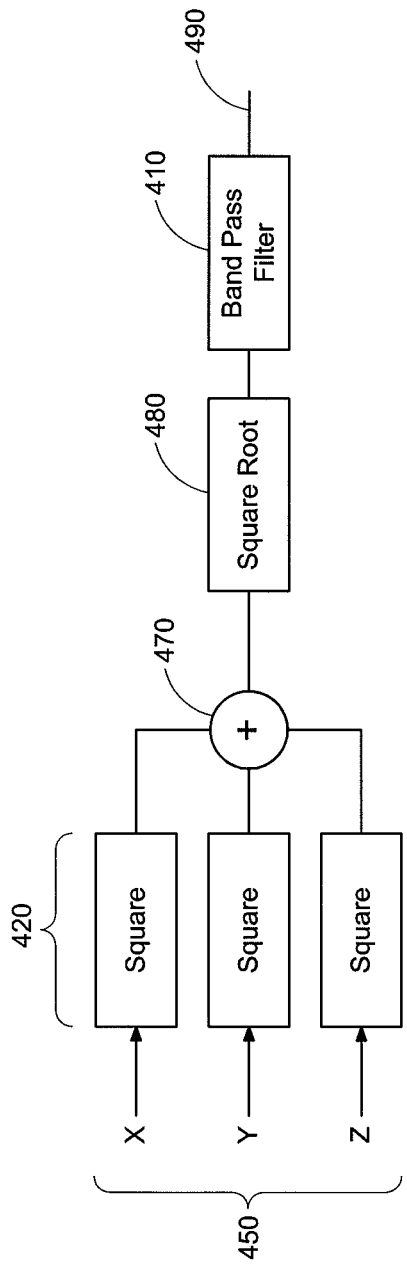
FIG. 5A is a block diagram depicting a third system for processing accelerometer data.

FIG. 5A is a block diagram depicting a third system for processing accelerometer data. The system in FIG. 5A is similar in some ways to that depicted in FIG. 4A. A manner in which the two systems differ is that the band pass filtering on the data is performed last. That is, the 3D accelerometer output 450 is squared using the squaring mechanisms 420, combined using a combination mechanism 470, the square root of combination is taken with the square root mechanism 480, and then finally a band pass filter is applied with the band pass filters 410 in order to produce filtered acceleration signal 490. In some embodiments, a system such as system is that depicted in FIG. 5A may require fewer band pass filters than the system depicted in FIG. 4A.

Figure 5B:
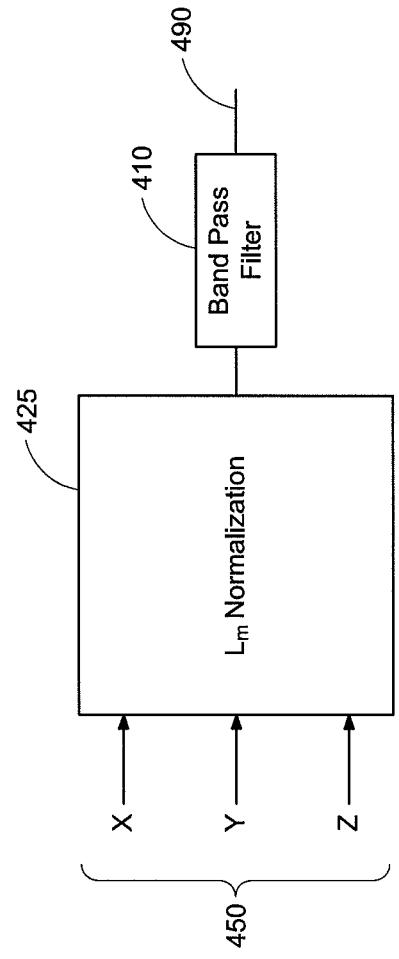
FIG. 5B is a block diagram depicting a fourth system for processing accelerometer data.

FIG. 5B is a block diagram depicting a fourth system for processing accelerometer data. The system in FIG. 5B is similar to that depicted in FIG. 4B in some ways and to that depicted in FIG. 5A in some ways. The system in FIG. 5A and in 5B both use a post-processing band pass filter, thereby, in some embodiments, requiring fewer band pass filters 410 in the system. The systems depicted in FIGS. 5B and 4B are similar in that each depicts a general $L_m$ normalization unit 425. As above, the choice of which value to use for "m" for the $L_m$ normalization unit 425 will depend on the situation and needs of the system, as will be recognized by the skilled artisan.

Embodiments such as those depicted in FIGS. 4A, 4B, 5A, and 5B may be implemented using an integrated circuit, a central processing unit, or any of many other options known to those skilled in the art. Referring FIG. 1, the system's depicted in FIGS. 4A, 4B, 5A, and 5B may be implemented within the signal processor 110, front-end interface 108, or any other appropriate module.

Figure 6:
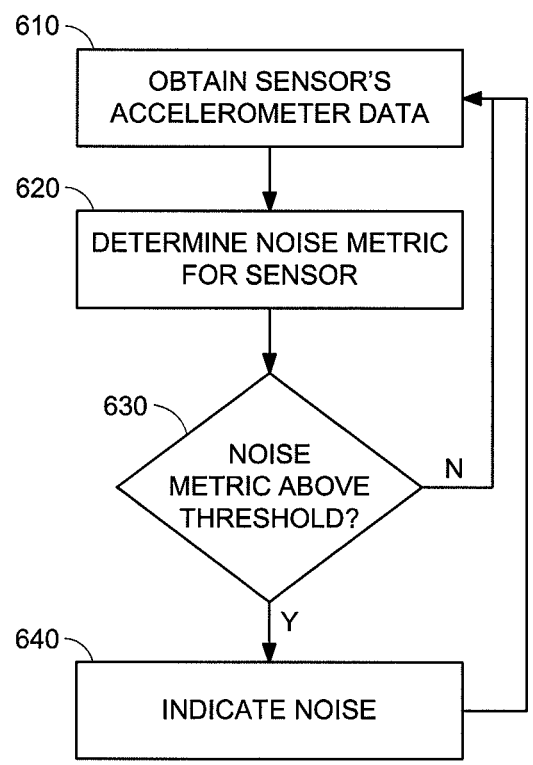
FIG. 6 is a flow chart depicting a process for indicating noise level for a signal obtained from the sensor device.

FIG. 6 is a flow chart depicting a process for indicating noise level for a signal obtained from the sensor device. For example, referring to FIG. 1, the signal obtained at sensor 101 and sent to device 103 may have noise in it. Sensor accelerometer 150A may provide useful information for determining how much noise is in the signal from sensor 101. Returning now to FIG. 6, in the first step, the sensor's accelerometer data is obtained. Accelerometer data is described elsewhere herein. After the accelerometer data is obtained in step 610, a determination is made as to potential noise in the signal based on accelerometer data in step 620. Some embodiments of processing of accelerometer data are described above with respect to FIGS. 4A, 4B, 5A, and 5B. In some embodiments, determining the noise metric may include subtracting out a gravity signal. Step 620 may include determining an overall measure of the accelerometer data, such as a single number that indicates the level of acceleration in the sensor. As discussed with respect to FIGS. 4A, 4B, 5A, and 5B, in some embodiments, determining a single number that indicates acceleration in the sensor may include squaring the incoming accelerometer data, summing the accelerometer data over multiple axes, passing the sum through a band pass filter, and/or performing $L_m$ normalization on the signal.

After a noise metric has been determined in step 620, then in step 630 a determination is made as to whether the noise metric is above a threshold. The noise threshold may be any appropriate number and may vary depending on the noise metric used. If it is determined in step 630 that the noise metric is above a certain threshold, then in step 640 noise is indicated to the user. The noise may be indicated in any number of ways. For example, in some embodiments, if the noise level is high, then there may be an indicator on the device that lights up or otherwise indicates that there is a high level of noise and that the signal received from the sensor should not be trusted. In some embodiments, if the noise level is above a certain threshold, then the graph indicating the received signal may be colored differently. In some embodiments, (not pictured) even if the noise level is below the threshold, then a low noise indication may be made on the device. For example, a red graph may indicate a high noise level, a green graph may indicate a low the noise level or no noise, and a yellow graph may indicate a noise level between high and low. In some embodiments, the data processing system may ignore data that is noisier than a certain threshold when calculating the level of the blood analyte. The calculation might be based solely on data received when the noise was below a certain threshold. Displaying movement feedback to the user wearing the sensor may be useful as the user will be made aware of even small movements of the sensor.

In some embodiments, after steps 610-640 have been performed, the cycle will repeat again starting in step 610.

Figure 7:
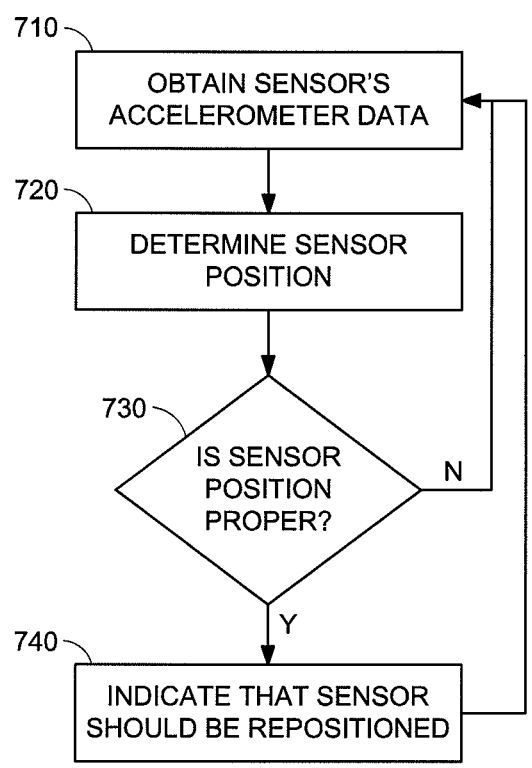
FIG. 7 is a flow chart depicting a process for prompting a patient to properly position and orient the sensor.

FIG. 7 is a flow chart depicting a process for prompting a patient to properly position and orient the sensor. In some embodiments, there is a proper position for the sensor that is on the patient's finger. This proper position for the sensor may be level or parallel with ground and below the patient's heart. In step 710, the sensor's accelerometer data is obtained. This is described above with respect to step 610. After the accelerometer sensor data has been obtained in step 710 then in step 720 a position is determined for the sensor. As is apparent to the skilled artisan, although accelerometer data cannot typically be used to determine position directly, it may be useful for estimating position based on the angle of the gravity vector and knowledge of the mechanics of the shoulder, elbow, wrist, and finger, for example. If an initial position is known, then the current position of the sensor may be estimated based on cumulative acceleration data. In some embodiments, the position may be estimated based on the 3 acceleration axes when the sensor is at rest. When the sensor is at rest, the value of acceleration in the three axes may indicate the direction of gravity. The resultant vector may be the gravity vector and define the orientation of the sensor.

After the sensor's position is determined in step 720, then in step 730 a determination is made as to whether the sensor's position is proper. In some embodiments, the sensor's position will be proper if it's within a broad range of positions, such as within 5°, 10°, or 30° of parallel with the ground and below the patient's heart.

If the sensor's position is not proper, as determined in step 730, then in step 740 an indication is made on the device connected to the sensor that the patient should reposition the sensor area. The indication to the patient to reposition the sensor could take any appropriate form. For example, in some embodiments, a text message may be displayed on the device indicating to the patient that he or she should "reposition the sensor to be parallel to the ground and below your heart." In some embodiments, a graphical indication may be made in order to show the patient that the sensor should be repositioned or show a picture of how the sensor should be repositioned.

After steps 710-740 have been performed, then in some embodiments, the cycle will begin again at step 710.

Figure 8:
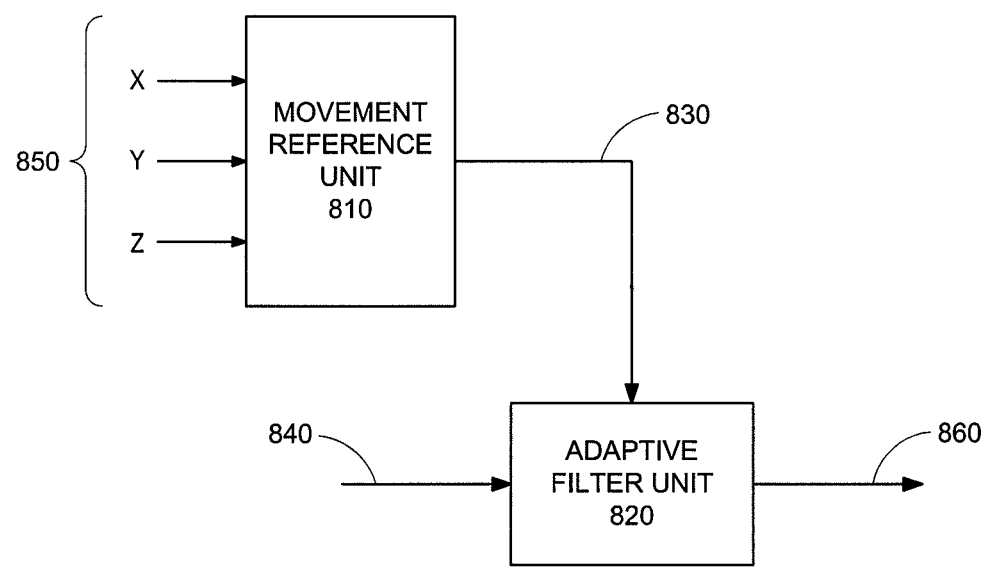
FIG. 8 is a block diagram depicting filtering of a noisy signal using information from a 3D accelerometer.

FIG. 8 is a block diagram depicting filtering of a noisy signal using information from a 3D accelerometer. In some embodiments, the output signal 850 from a 3D accelerometer is received at a movement reference unit 810. The movement reference unit 810 produces a noise reference signal 830. Examples of producing a noise reference signal are described in FIGS. 4A, 4B, 5A, 5B, and 9. An adaptive filter unit 820 receives the noise reference signal 830 and the plethysmograph signal 840. The adaptive filter unit 820 processes the plethysmograph signal 840 along with the noise reference signal 830 in order to produce the noise-reduced signal 860.

In some embodiments, movement reference unit 810 and adaptive filter unit 820 may be implemented as part of a signal processor 110 of FIG. 1 or using other appropriate computers, circuitry, or computational device. Accelerometer output signal 850 may be produced by an accelerometer 150A or front-end interface 108.

Figure 9:
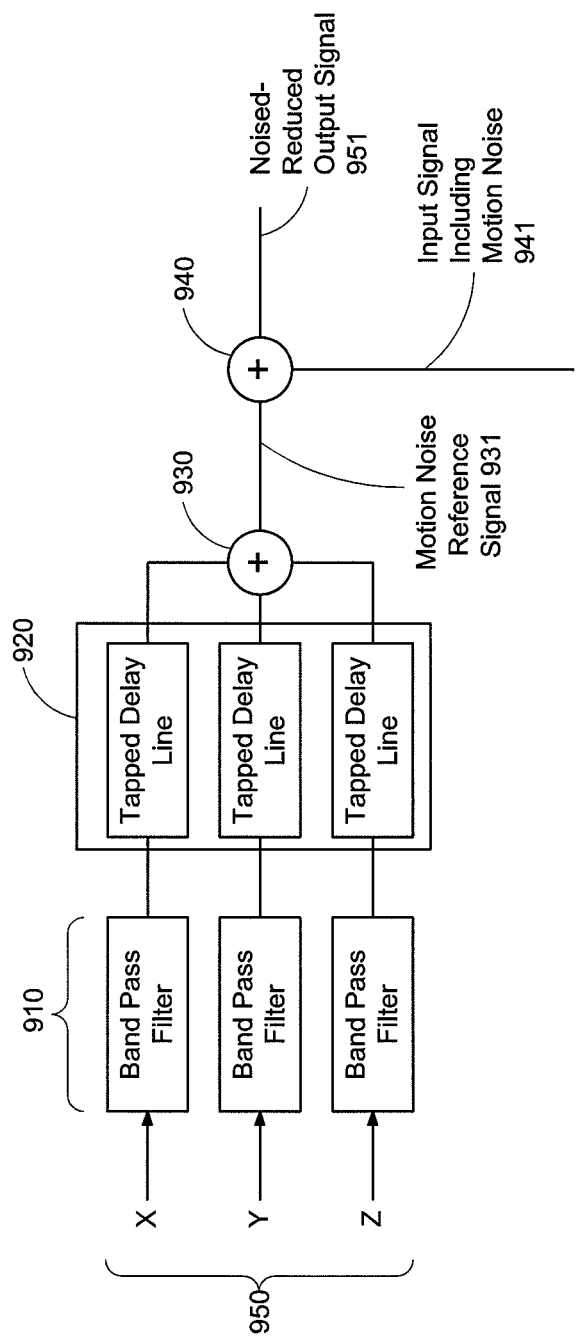
FIG. 9 is a block diagram depicting a system for subtracting a noise signal from an input signal.

FIG. 9 is a block diagram depicting a system for subtracting a noise signal from an input signal. The system in FIG. 9 takes as input the accelerometer data 950 and applies a band pass filter 910 on the accelerometer data 950. The system of FIG. 9 also applies a tapped delay line to the accelerometer data 950. A tapped delay line 920 may be a delay line with at least one "tap." A delay-line tap extracts a signal output from somewhere within the delay line, optionally scales it, and may sum with other taps for form an output signal. A tap may be interpolating or non-interpolating. A non-interpolating tap extracts the signal at some fixed delay relative to the input signal.

The output of the tapped delay lines 920 are combined in combination mechanism 930, which may be similar to combination mechanism 470 described above. The resultant motion noise reference signal 931 may then be combined with the input signal 941, which includes motion noise. In some embodiments, the result of combining these two signals is that the motion noise, as represented by the motion noise reference signal 931, is subtracted out of the input analyte measurement signal 941, to produce a motion-noise reduced output signal 951.

Returning now to FIG. 1, in some embodiments, one or more accelerometers, such as accelerometer 150B, may be associated with device 103. In some of those embodiments, the output of accelerometer 150B and any other accelerometers may be used to produce effects at the user interface 112. For example, in one embodiment, if a user moves or shakes the device 103, then device 103 may power up, show the user a subsequent menu, reorient the display, or provide other information.

In some embodiments, one or more accelerometers, such as accelerometer 150A, are associated with sensor 101. The signal processor 110 may determine an orientation of sensor 101 based on information from accelerometer 150A. If, for example, the orientation of sensor 101 were important for the operation of the sensor 101 or the quality of the signal produced by the sensor 101, then the signal processor's 110 determination of orientation could be used to output feedback to the user via the user interface 112. For example, if holding the sensor 101 relatively motionless and parallel to the ground were important and the user was moving the sensor 101 and not holding it in the correct orientation, then the user interface 112 could indicate to the user that the sensor should correct the orientation or movement of the sensor 101.

The processes, computer readable medium, and systems described herein may be performed on various types of hardware, such as hand-held devices or computer systems. Hand-held devices may include personal data assistants, cell phones, portable music players, laptops, and any other portable computing device. Computer systems and hand-held devices may include a bus or other communication mechanism for communicating information, and a processor coupled with the bus for processing information. A hand-held device or computer system may have a main memory, such as a random access memory or other dynamic storage device, coupled to the bus. The main memory may be used to store instructions and temporary variables. The computer system may also include a read-only memory or other static storage device coupled to the bus for storing static information and instructions. The hand-held device or computer system may also be coupled to a display, such as a CRT or LCD monitor. Input devices may also be coupled to the computer system. These input devices may include a mouse, a trackball, or cursor direction keys. Computer systems or hand-held device described herein may include instrument 140, patient monitor 120, photocommunicative key 210, information module 370, and refill module 310. Each computer system may be implemented using one or more physical computers or computer systems or portions thereof. The instructions executed by the hand-held device or computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A physiological monitoring system including an optical sensor configured to be applied to a finger of a patient, the monitoring system comprising:

said optical sensor including (i) a housing configured to position sensor components proximate tissue of a measurement site on said finger, (ii) at least one accelerometer outputting position signals usable by a patient monitor to estimate a position of the sensor with respect to the patient to provide feedback to the user through a user interface of said patient monitor on how to properly position the sensor with respect to the patient to improve measurement accuracy, (iii) at least one light source, (iv) and at least one photodetector configured to detect light from said light source after attenuation by said tissue of said measurement site of said patient and output physiological signals usable by the patient monitor to determine measurements of one or more physiological characteristics of the patient; and said patient monitor configured to receive said position signals and said physiological signals over a plurality of monitoring cycles, said patient monitor comprising one or more hardware processors configured to process said position signals continuously and automatically over the plurality of monitoring cycles to estimate said position of the optical sensor with respect to level and with respect to the patient's heart, determine from the estimated position when the optical sensor is positioned above the patient's heart and more than 30 degrees from level, and provide said feedback to said user to reorient said finger based on said determination during the plurality of monitoring cycles, said monitor also configured to process said physiological signals to determine said measurements, wherein said monitor includes a display and said monitor configured to provide said feedback includes being configured to output indicia to said display responsive to said sensor's position to guide a caregiver or said patient on repositioning said sensor within 30 degrees from level and below the patient's heart with respect to the patient to improve said accuracy of said measurements.

2. The physiological monitoring system of claim 1, wherein said optical sensor comprises a tissue shaper.

3. The physiological monitoring system of claim 1, wherein the optical sensor comprises a memory and light source drivers.

4. The physiological monitoring system of claim 1, wherein said indicia comprises an indication to the patient to reposition said sensor below heart of said patient.

5. The physiological monitoring system of claim 1, wherein said indicia comprises an indication to the patient to reposition said sensor to level to improve said accuracy of said measurements.

6. The physiological monitoring system of claim 1, wherein said with respect to level comprises within 10 degrees from level.

7. The physiological monitoring system of claim 1, wherein said with respect to level comprises within 5 degrees from level.

8. The physiological monitoring system of claim 1, wherein said indicia comprises graphical information.

9. A method of properly positioning a noninvasive optical sensor with respect to a heart of a patient to improve an accuracy of measurement values determined by processing signals from said optical sensor, the method comprising:

receiving position signals over a plurality of monitoring cycles from one or more accelerometers housed proximate said optical sensor;

receiving physiological signals over the plurality of monitoring cycles from at least one detector configured to detect light attenuated by a tissue of a finger of said patient;

processing said position signals to estimate a position of the optical sensor with respect to level and with respect to the patient's heart;

determining automatically and continuously over the plurality of monitoring cycles using one or more hardware processors, from the estimated position when the optical sensor is positioned above the patient's heart;

determining automatically and continuously over the plurality of monitoring cycles using one or more hardware processors, from the estimated position when the optical sensor is positioned more than 30 degrees from level;

providing a feedback to said user to reorient said finger based on said determination that the estimated position of the optical sensor is above the patient's heart and said determination that the estimated position of the optical sensor is more than 30 degrees from level;

processing said physiological signals to determine measurements of one or more physiological characteristics of the patient, wherein said providing said feedback includes outputting indicia to a display responsive to said sensor's position to guide a caregiver or said patient on repositioning said sensor within 30 degrees from level and below the patient's heart with respect to the patient to improve said accuracy of said measurement values.

10. The method of claim 9, wherein said indicia comprises an indication to the patient to reposition said sensor to level to improve said accuracy of said measurement values.

11. The method of claim 9, wherein said with respect to level comprises within 10 degrees from level.

12. The method of claim 9, wherein said with respect to level comprises within 5 degrees from level.

13. The method of claim 9, wherein said providing said indicia comprises a graphical information.

* * * * *